United States Patent [19]

Wilcox

[11] Patent Number: 6,096,759
[45] Date of Patent: *Aug. 1, 2000

[54] METHOD FOR TREATING ESSENTIAL HYPERTENSION

[75] Inventor: Christopher S. Wilcox, Great Falls, Va.

[73] Assignee: Georgetown University, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/933,379

[22] Filed: Sep. 19, 1997

[51] Int. Cl.$^7$ .................................................. A61K 31/445
[52] U.S. Cl. ............................................................ 514/315
[58] Field of Search ................................................ 514/315

[56] References Cited

U.S. PATENT DOCUMENTS

| | | | |
|---|---|---|---|
| 4,046,901 | 9/1977 | Nedelec et al. | 424/267 |
| 5,034,395 | 7/1991 | Tamada et al. | 514/277 |
| 5,332,577 | 7/1994 | Gertner . | |
| 5,462,946 | 10/1995 | Mitchell et al. | 514/315 |
| 5,516,881 | 5/1996 | Lee et al. | 528/320 |
| 5,541,163 | 7/1996 | Lavall''e et al. | 514/19 |
| 5,543,422 | 8/1996 | Coutts et al. | 514/319 |
| 5,591,710 | 1/1997 | Hsia | 514/6 |
| 5,622,994 | 4/1997 | Carney et al. | 514/643 |
| 5,725,839 | 3/1998 | Hsia | 424/9.33 |
| 5,741,893 | 4/1998 | Hsia | 30/385 |
| 5,767,089 | 6/1998 | Hsia | 514/21 |
| 5,804,561 | 9/1998 | Hsia | 514/21 |
| 5,807,831 | 9/1998 | Hsia | 514/21 |

FOREIGN PATENT DOCUMENTS

WO 92/22290   12/1992   WIPO .

OTHER PUBLICATIONS

Tab, Neuroreport 7 (8) 1382–4 May 31, 1996.
Karmeli et al, GUT, 38(6) 826–31 Jun. 1996.
Monte et al, Free Radical Biol. Med., 21(4) 463–470 1996.
C.J. Bulpitt et al., "Vitamin C and blood pressure," *J. Hypertens,* 8(12):1071–5 (1990).
D. Giugliano et al., "Diabetes Mellitus, hypertension, and cardiovascular disease: which role for oxidative stress?." *Metabolism* 44(3):363–8 (1995).
S. Grunfeld et al., "Role of Superoxide in the depressed nitric oxide production by the endothelium of genetically hypertensive rats," *Hypertension* 26(6 Pt 1):854–7 (1995).
R.J. Gryglewski et al., "Superoxide anion is involved in the breakdown of endothelium—derived vascular relaxing factor," *Nature* 320(6061): 454–6 (1986).

D.G. Harrison et al., "Physiologic consequences of increased vascular oxidant stresses in hypercholesterolemia and atherosclerosis: implications for impaired vasomotion," *Am. J. Cardiol* 75(6): 75B–81B (1995).
V.V. Khramtsov et al., "In vitro and in vivo studies of the derivatives of 1,2–diazetine and nitronylnitroxide as donors and acceptors of nitric oxide," *Biokhimiya,* 61(10): 1731–1742 (1996).
K.V. Kumar et al., "Are free radicals involved in the pathobiology of human essential hypertension?," *Ree Radic Res Commun.* 19(1): 59–66 (1993).
J. M. McCord, "Oxygen–derived free radicals in postischermic tissue injury," *N. Engl. J. Med.* 312(3): 159–63 (1985).
Y. Miyamoto et al., "Potentiation of nitric oxide–mediated vasorelaxation by xanthine oxidase inhibitors," *Proc. Soc. Exp. Biol. Med.* 312(4): 366–373 (1996).
K. Nakazono et al., "Does superoxide underlie the pathogenesis of hypertension?" *Proc. Natl. Acad. Sci. USA* 88: 10045–10048 (1991).
G.M. Rubanyi et al., "Superoxide anions and hyperoxia inactivate endothelium–derived relaxing factor," *Am. J. Physiol.* 250: H822–H827 (1986).
C.G. Schnackenberg et al., "Normalization of blood pressure and renal vascular resistance in SHR with a membrane–permeable superoxide dismutase mimetic," *Hypertension,* 32(1): 59–64 (1998).
C.G. Schnackenberg et al., "Long–term tempol administration attenuates the hypertension and production of 8–iso prostaglandin F2a in SHR." *Hypertension* 32(3): 622 (1998).
H. Suzuki et al., "In vivo evidence for microvascular oxidative stress in spontaneously hypertensive rats, Hydroethidine microfluorography," *Hypertension* 25(5): 1083–1089 (1995).
M.R. Tschudi et al., "Direct in situ measurement of nitric oxide in mesenteric arteries. Increased decomposition by superoxide in hypertension." *Hypertension* 27(1): 32–35 (1996).
W.Y Tse et al., "Antioxidant status in controlled and uncontrolled hypertension and its relationship to endothelial damage." *J. Hum. Hypertens.* 89:843–849 (1994).
M. Yoshioka et al., "Effects of ascorbic acid on blood pressure and ascorbic acid metabolism in spontaneously hypertensive rates (SH Rats)." *Internat. J. Vit. Nutr. Res.* 55:301–307 (1985).

*Primary Examiner*—Rebecca Cook
*Attorney, Agent, or Firm*—Morgan, Lewis & Bockius LLP

[57] ABSTRACT

This invention relates to the treatment of essential hypertension by administration of anti-hypertensive effective amounts of 4-hydroxy-2,2,6,6-tetramethyl-1-piperidine-1-oxyl (tempol).

10 Claims, No Drawings

METHOD FOR TREATING ESSENTIAL HYPERTENSION

The work leading to this invention was partially funded by the United States Government under NIH grants DK 36079 and DK 49870.

FIELD OF THE INVENTION

This invention relates to the treatment of essential hypertension by administration of anti-hypertensive effective amounts of 4-hydroxy-2,2,6,6-tetramethyl-1-piperidine-1-oxyl (TEMPOL).

BACKGROUND OF THE INVENTION

Most, although not all, studies have demonstrated blunted agonist-stimulated, endothelium-dependent vasorelaxation in the peripheral circulation of patients with essential hypertension. This suggests blunted release of endothelium-dependent relaxation factor (EDRF) or enhanced generation of endothelium-dependent contraction factor (EDCF). In the isolated aorta, there are impaired endothelium-dependent relaxation responses in spontaneously hypertensive rats (SHR) compared to their genetically normotensive controls. This has been attributed to an EDCF, which can inactivate nitrogen oxide (NO). The precise identity of EDCF remains unclear, but its generation and action depend on cyclooxygenase and thromboxane (Tx) $A_2$/prostaglandin (PG) $H_2$ receptors and its actions can be prevented by blockade of oxygen free-radicals ($O_2^-$). $O_2^-$ and NO interact to produce peroxynitrite, which effectively inactivates physiologic concentrations of NO.

However, in contrast to the aorta, coronary artery endothelium-dependent vasodilation is normal in the SHR heart and there is enhanced release of NO from the perfused SHR heart and enhanced activity of constitutive endothelial cell type (ec) nitric oxide synthase (NOS) in cardiac endothelium of SHR. Thus, organs differ in their regulation of NO generation in genetic hypertension.

Studies in isolated kidneys have shown an enhanced calcium-dependent, constitutive NOS activity in the renal medulla of the SHR and a normal or enhanced endothelium-dependent vasodilator response to bradykinin (Bk) or acetylcholine (Ach). These effects are mediated via NO and endothelium-dependent hyperpolarization factor (EDHF). There is also a normal or enhanced rate of excretion of the NO metabolites nitrite ($NO_2$) and nitrate ($NO_3$) from isolated kidneys of SHR and an enhanced basal vasodilator tone mediated by NO in the hydronephrotic kidney of the SHR. The perfused kidney from the SHR also generates an EDCF whose effects oppose the vasorelaxant effects of locally generated EDRF-NO. Afferent arterioles isolated from SHR and perfused in vitro have an enhanced vasoconstrictor response to blockade of NOS with L-NMA. However, in contrast to these results in isolated kidneys or vessels that generally suggest a well-maintained or enhanced NO generation, studies in intact SHR kidneys suggest a diminished role for NO in tubular and vascular regulation. Thus, SHR have impaired pressure natriuresis that may depend on diminished NO since it can be corrected by infusion of L-arginine. They also have enhanced TGF responses that have been ascribed to diminished macula densa-derived NO since there is a blunted response to local microperfusion of nitro-L-arginine (L-NA) into the macula densa. Any defect in NO generation in the juxtaglomerular apparatus (JGA) of the SHR could contribute to heightened TGF responses, enhanced renal vascular resistance (RVR), salt retention, and hypertension.

Recently, it has been shown that microperfusion of nitro-L-arginine (L-NA) into the macula densa enhances TGF responses more in Wistar-Kyoto rats (WKY) than SHR rats.

Dissociation between NOS expression and function in the JGA is seen in Sprague-Dawley rats during changes in salt intake. Dietary salt restriction enhances bNOS mRNA and protein expression in macula densa yet abolishes the enhancement of TGF by local microperfusion of L-NMA into the JGA. In the salt-restricted Sprague-Dawley rat, microperfusion of L-arginine into the JGA blunts TGF and restores a response to microperfusion of L-NMA into the JGA. This effect of L-arginine is presumably due to providing substrate for macula densa NOS since its effects are stereospecific and are prevented by inhibition of NOS with L-NMA.

Tempo, or its 4-hydroxy derivative, Tempol, protects beating cardiomyocytes against oxidative damage in vitro and protects the heart against reperfusion damage in vivo. Retrograde microperfusion of Tempo directly into the macula densa consistently and reversibly blunted TGF responses in both SHR and WKY rat nephrons. This suggests that $O_2^-$ may be formed in the JGA of both hypertensive and control rats and modulate the TGF responses, consistent with the finding of EDCF responses in the renal vessels of SHR and WKY. Despite the high renal blood flow, and the high $O_2$ tension in renal venous blood, the cells of the renal cortex appear to be quite hypoxic because of a pre-glomerular $O_2$ shunt resulting in values for $PO_2$ at surface tubules that cycle around 35 mm Hg. It has been argued that the macula densa cells, being downstream from the highly metabolically active thick ascending limb cells, are normally in a $O_2$-compromised environment and that TGF prevents nephron $O_2$ deficiency.

SUMMARY OF THE INVENTION

The treatment of essential hypertension has long presented a serious problem to the medical profession. It is now found that administration of 4-hydroxy-2,2,6,6-tetramethyl-1-piperi-dine-1-oxyl (TEMPOL) in dosage of from 10 to 300 mg/kg/day will result in lowering of the blood pressure. Compositions containing anti-hypertensive effective amounts of TEMPOL in pharmaceutically acceptable carriers may be administered parenterally, orally or transdermally.

DESCRIPTION OF THE INVENTION

It is the purpose of this invention to provide means of controlling essential hypertension by administration of TEMPOL. It is also the purpose of this invention to provide compositions appropriate for dosing with TEMPOL. To evaluate the recent finding that an absent TGF response to NOS blockade in the salt-restricted Sprague-Dawley rat could be restored by local microperfusion of L-arginine into the JGA, several studies were performed. As a part of the study defective NO action in the JGA of SHR was assessed from the TGF response to microperfusion of the low molecular weight nitroxide, 2,2,6,6-tetramethyl-1-piperidinyloxy (Tempol). TEMPOL is a nonmetal, cell membrane-permeable superoxide dismutase (SOD) mimetic that can protect against cardiac reperfusion damage or cardiomyocyte oxidative damage.

Methods

Studies were undertaken on male SHR and WKY, weighing 235–300 g, and maintained on a standard rat chow (Purina Rat Chow, St. Louis, Mo.) with a sodium content of 0.3 g. 100 $g^{-1}$. They were allowed free access to food and water until the day of study.

Series 1: RT-PCR analysis of mRNA abundance of ecNOS and bNOS transcripts in glomeruli or renal cortex of SHR and WKY. These studies were designed to test the hypothesis that transcripts for constitutive NOS are diminished in the cortex of the SHR. bNOS transcripts and protein are expressed abundantly in the macula densa of the renal cortex, and previous studies have shown a close correlation between bNOS mRNA transcript abundance in renal cortex and bNOS transcript abundance in isolated macula densas. Accordingly, studies of bNOS mRNA expression were undertaken in outer cortical tissue with the assumption that differences likely reflect changes predominantly in macula densa bNOS MRNA. ecNOS MRNA is more widely expressed in the vasculature and therefore its abundance was assessed in individual glomeruli that were microdissected from outer cortical nephrons.

Under thiobarbital anesthesia (pentobarbital 100 mg·kg$^{-1}$ ip), the abdomen was opened and the aorta cannulated to allow flushing of the kidneys with ice-cold dissection solution. This fluid contained 135 mM NaCl, 1 mM $Na_2HPO_4$, at pH 7.4. For isolation of outer cortical kidney RNA, one kidney from 6 SHR and one from 6 WKY was cut longitudinally and a segment of outer cortex removed and digested with collaginase (1%) for 30 min at 37° C. Glomeruli were dissected under a stereomicroscope in rinse solution at 4° C. This contained (200 µl volume): 170 µl dissection solution, 20 µl of 5 µM DIT, 10 µl of 10 mM vanadyl riboneucleoside complex. Dissected glomeruli were further cleaned in rinse solution II under stereomicroscope at 4° C. This contained (200 µl volume): 170 µl dissection solution, 20 µl of 5 µm of DIT, and 10 mM of 2U/µl RNA sin+. Finally, glomeruli were transferred to centrifuge tubes containing lysis solution. This contained (200 µl volume): 166 µl deionized water, 4 µl of 2% Triton X-100, 20 µl of 5 mM DTT, and 10 µl of 2U/µl RNA sin+. Total RNA was extracted using RNA ATAT-60™ (Tel-test B, Inc., Friendswood, Tex.). The mRNA was reverse transcribed (RT) with Oligo (dT)$_{16}$ as primer and MULV reverse transcriptase using an RNA PCR Kit (Perkin Elmer, Inc., Branchburg, N.J.). The primers used for PCR of the bNOS gene product were those described previously. For bNOS, the sense primer was: 5'-GTCGAATTCCGAATACCAGCCTGATCCATGGAA-3' (Seq. #1), and the antisense primer was 5'-CGCGGATCCCATGCGGTGGACTCCCTCCTGGA-3' (Seq. #2). The predicted product had a length of 599 base pairs. Beta-actin was selected as a "housekeeper gene" for comparison. The primers used for β-actin mRNA were: sense primer 5'-GATCAAGATCATTGCTCCTC-3' (Seq. #3) and antisense primer: 5'-TGTACAATCAAAGTCCTCAG-3' (Seq. #4). The PCR product had a predicted length of 426 bp. The amounts of NOS cDNAs were normalized by the amounts of β-actin cDNA. The reaction mixture contained 50 pmol of each primer, 1.25 mM deoxynucleotide mixture, 2.5 µl Taq DNA polymerase, 10 mM Tris-HCl (pH 10), 50 mM KCl, 1.5 mM $MgCl_2$, 0.001% (w/v) gelatin in a final volume of 50 µl. The PCR was carried out by the following protocol: after an initial melting temperature of 94° C. for 4 min, there was 30 sec of denaturation at 94° C., 45 sec of annealing at 60° C., and 45 sec of extension at 72° C. for repeated cycles of amplification, followed by a final extension at 72° C. for 7 min. The PCR product was analyzed on a 1.5% agarose gel stained with ethidium bromide and visualized under UV light. The size of the products were compared to a rat kidney cDNA probe for bNOS. To verify the authenticity of the PCR products, the amplified bNOS cDNAs from the rat kidney cortex of an SHR and WKY rat were purified by MICROCON™ (Amicon Co., Beverly, Mass.) and sequenced with an AmliTaq cycle sequencing kit (Perkin Elmer, Inc., Branchburg, N.J.).

Transcript abundance for ecNOS was assessed in single outer cortical glomeruli, isolated using the method of Pelayo et al. Separate groups of SHR (n=6) and WKY (n=6) were prepared as described above. For these studies, mRNA abundance was examined per single glomerulus. After anesthesia and preparation of the animal, blue 1–5 µm latex microspheres (Polysciences, Warrington, Pa.) were infused in HEPES buffer (pH 7.4) into the left kidney. After perfusion, the kidney was excised, cut into coronal slices, placed on ice, and a glomerulus from the outer cortex microdissected under stereomicroscopy. Thereafter, the mRNA was extracted, reverse transcribed, and amplified as described above. The primers used for ecNOS were: sense primer 5'-GTCGAATTCCTGGCGGCGGAAGAGAAGGAGTC-3' (Seq. #5) and antisense: 5'-CGCGGATCCGGGGCTGGGTGGGGAGGTGATGTC-3' (Seq. #6). The predicted product had a length of 691 base pairs and was compared to a rat kidney cDNA probe for ecNOS from our laboratory.

Care was taken to optimize conditions for the RT-PCR. For each study, parallel analyses were undertaken of serially diluted amounts of cDMA to ensure that product (as assessed by densitometry) increased log-linearly with cDNA amount in the ranges used. Negative controls were undertaken by PCR without prior RT, and by RT-PCR of the buffer used.

Series 2: Comparison of ecNOS, bNOS, and INOS protein expression in kidneys of SHR and WKY. These studies were undertaken to assess the hypothesis that changes in renal cortical gene transcript abundance were accompanied by changes in gene translation product. Six SHR and six WKY rats were anesthetized and their kidneys prepared as described above. Slices of kidney outer cortex were dissected and homogenized on ice in 1 ml buffer containing 20 mm Tris pH 7.2, 0.5 mM EDTA, 0.5 mM EGTA, 1 mM leupeptin, 1 mM DDT, 0.1 mM phenylmethylsulfonyl fluoride using a Potter-Elvehjem Teflon glass tissue homogenizer. Homogenates were sonicated three times for 40 sec, centrifuged at 12,000 g for 15 min, and diluted in sodium dodecyl sulfate (SDS) buffer (0.5 M TRIS-HCl pH 6.8, 20% (v/v) glycerol, 4.6% (w/v) SDS). A sample was prepared to contain 350 Ag protein and was applied to an 8% SDS gel. Proteins were separated by SDS-PAGE and electroblotting to a nitrocellulose membrane (Pierce, Rockford, Ill.) that was stained by Ponceau solution to ascertain that protein transfer to the membrane was complete. The nitrocellulose membranes were incubated with 3% nonfat dry milk in Tris-buffered saline with 0.1% Tween-20 (TBST) for 1 h, followed by overnight incubation with a mouse monoclonal antibody for bNOS, iNOS, or ecNOS in a 1:400 dilution. After rinsing in TBST, membranes were incubated for 1 h with anti-mouse IgG antibody conjugated horseradish peroxidase at a 1:1000 dilution. They were then rinsed with TBST, and bNOS, INOS, or ecNOS protein was detected by diaminobenzidine (DAB) with 0.3% hydrogen peroxide.

Series 3: Immunohistochemical study of ecNOS and bNOS distribution in the kidney of SHR and WKY. These studies were undertaken to assess the distribution of ecNOS immunoreactivity in vascular and glomerular capillary endothelium and bNOS in macula densa cell cytoplasm in SHR and WKY rats. After anesthesia, the abdominal aorta of 5 SHR and 5 WKY was cannulated and the kidneys perfused with 0.154 M NaCl followed by paraformaldehyde lysine periodate (PLP) solution for 5 min, cut into slices, and immersed into PLP overnight at 4° C. before embedding in wax (polyethylene glycol 400 disterate; Polysciences, Inc., Warrington, Pa.) or paraffin.

Two $\mu$m wax sections were processed for light microscopic immunohistochemistry using the streptavidin-biotin-horseradish peroxidase complex technique (LSAB kit, Dako, Calif.). Briefly, sections were dewaxed, rehydrated, and incubated with 3% $H_2O_2$ for 10 min to eliminate endogenous peroxidase activity. After rinsing in Tris-buffered saline with 0.1% Tween 20 (TBST), sections were treated with blocking serum for 10 min and incubated with primary mouse monoclonal antibody in a dilution of 1:100 for bNOS and ecNOS (both from Transduction Laboratories Inc., Lexington, Ky.) for 1 h. After rinsing with TBST, the sections were incubated with the secondary antibody, biotinylated rabbit polyclonal antibody against mouse immunoglobin (Dako, Denmark), in a dilution of 1:600 for 30 min, rinsed, and incubated for 20 min with horseradish peroxidase (HRP) labeled streptavidin. After rinsing with TBST, HRP was detected by diaminobenzidine (DAB) with hydrogen peroxide. The sections were counterstained with hematoxylin and examined under light microscopy.

For electron-microscopic (EM) immunocytochemistry using the post-embedding imunogold procedure, one $mm^3$ blocks of kidney cortex were dehydrated and embedded in Lowicryl. Ultrathin sections were cut on an ultramicrotome, mounted on colloidin-coated nickel grids, and processed for immunogold labelling. The sections were incubated with 0.1 M $NH_4Cl$ for 1 h, rinsed with buffer solution (0.02 M Tris HCl, 0.15 M NaCl, 0.05% Iween 20, adjusted to pH 7.2) for 15 min, and incubated with mouse monoclonal antibody against ecNOS (Transduction Laboratories Inc., Lexington, Ky.) at a concentration of 1:100 overnight at 4° C. After three 10-min buffer washes, 30 nm gold-labelled goat anti-mouse IgG secondary antibody (Amersham Life Science, Buckinghamshire, U.K.) was applied for 2 h at a dilution of 1:50. Thereafter, the sections were washed with buffer, incubated with 2% glutaraldehyde/PBS solution for 30 min, rinsed with distilled water, counterstained with uranyl acetate and lead citrate, and examined with an electron microscope (Hitachi 7000 transmission electron microscope). In order to evaluate semi-quantitatively the degree of ecNOS immunogold labelling, a blinded observer assessed EM pictures of sections from 3 SHR and 3 WKY rats. The number of immunogold particles detected overlying epithelial cells were counted and expressed as the number of particles/$\mu$n of glomerular basement membrane.

Series 4. Effects of inhibition of bNOS on maximal TGF responses in SHR and WKY. These experiments were designed to test whether the enhanced TGF of the SHR kidney is due to a blunted generation of NO by bNOS in the macula densa. Groups of SHR and age-matched WKY rats were prepared for in vivo micropuncture, microperfusion, and TGF studies as described in detail previously. In brief, animals were anesthetized with thiobarbital (Inactin, 100·mg $kg^{-1}$; Research Biochemicals, Inc., Natick, Mass.). A catheter was placed in a jugular vein for fluid infusion and in a femoral artery for recording of mean arterial pressure (MAP) from the electrically damped output of a pressure transducer (Statham, Inc.). A tracheotomy tube was inserted and the animals were allowed to breathe spontaneously. The left kidney was exposed by a flank incision, cleaned of connective tissue, and stabilized in a Lucite cup. This kidney was bathed in 0.154 M NaCl maintained at 37° C. After completion of surgery, rats were infused with a solution of 0.154 M NaCl and 1% albumin at 1.5·ml·$h^{-1}$ to maintain a euvolemic state. Micropuncture studies were begun after 60 min for stabilization.

For orthograde microperfusion of the loop of Henle (LH), a micropipette (8 $\mu$m OD) containing artificial tubular fluid (ATF) stained with FD&C dye was inserted into a late proximal tubule. Injections of the colored ATF identified the nephron and the direction of flow. An immobile bone wax block was inserted into this micropuncture site via a micropipette (10–15 $\mu$m) connected to a hydraulic drive (Trent Wells, Inc., LaJolla, Calif.) to halt tubular fluid flow. A perfusion micropipette (6–8 $\mu$m) containing ATF with test compounds or vehicle was inserted into the proximal tubule downstream from the wax block and connected to a nanoliter perfusion pump (WPI, Sarasota, Fla.). A pressure micropipette (1–2 $\mu$m) was inserted into the proximal tubule upstream from the wax block to measure proximal stop flow pressure (PSF). Changes in PSF are an index of changes in glomerular capillary hydraulic pressure ($P_{GC}$). Measurements of PSF were made in each nephron during zero loop perfusion and during perfusion with ATF at 40 nl·$min^{-1}$, which produces a maximal TGF response, defined as the difference between PSF values recorded during perfusion of the loop with ATF at 0 and 40 nl·$min^{-1}$.

The maximal TGF responses were determined in SHR (n=4) and WKY rats (n=4) to perfusion of the LH with ATF+vehicle and contrasted with the maximal TGF responses during perfusion with ATF+7-nitroindazole (7-NI; $10^{-4}$ M).

Series 5: Maximal TGF responses during microperfusion of L-arginine in SHR and WKY. This series was designed to test the effect of a reduced delivery of L-arginine to the macula densa on NO generation, as assessed in Series 4. Groups of SHR (n=4) and WKY rats (n=3) were prepared for microperfusion. PSF was recorded during orthograde LH perfusion at 0 and 40 nl·$min^{-1}$ with ATF+vehicle and ATF+L-arginine ($10^{-3}$ M). (Previous studies had shown that this was a maximally effective dose.)

Series 6: Effects on maximal TGF responses of microperfusion of Tempol into the JGA of SHR and WKY. The purpose of this example was to determine whether oxygen-derived free-radicals in the JGA potentiated TGF in the SHR. Groups of SHR (n=5) and WKY rats (n=5) were prepared for studies of retrograde microperfusion into the macula densa. As anticipated from its high membrane permeability, TEMPOL had rather inconsistent results when perfused orthogradely from the late proximal tubule. Therefore, these studies of TGF were conducted with retrograde microperfusion from the early distal (ED) tubule into the macula densa. After identifying the nephron with FD&C green, the last proximal convolution was vented and a wax block placed upstream. A micropipette (8–10 μm OD) was inserted into the ED tubule upstream from an oil droplet. The loop of Henle was perfused retrogradely with perfusate entering the macula densa segment directly at 0 and 20 nl·min$^{-1}$. This represents a maximal activation for TGF by retrograde perfusion. Preliminary studies indicated that a dose of Tempol of 10$^{-3}$ M was maximally effective, and the effects were reversible. Therefore, this dose was used thereafter in the test animals. (Dosage/kg would usually be lower in larger animals.) Comparisons were made of maximum TGF responses obtained during perfusion of ATF+vehicle (ethanol) and ATF+Tenpol.

Statistical Methods

Values are reported as mean±SEM. An analysis of variance (ANOVA) was applied to the within-group data for SHR and WKY; where appropriate, post hoc Dunnett's t tests were applied thereafter. Values were taken as statistically significant at p<0.05.

Results

For Series 1, ecNOS mRNA abundance was consistently greater in outer cortical glomeruli from SHR than WKY, although similar densities were apparent for β-actin mRNA. This was confirmed by densitometric analysis. The cDNA obtained from one glomerulus was analyzed and found to correspond fully with the published sequence for rat ecNOS.

RT-PCR products corresponding to cDNAs for bNOS were obtained from outer cortex of 6 SHR and 6 WKY rat kidneys. The density of the bands obtained from SHR was consistently greater than that for WKY, although similar densities were apparent for β-actin. This difference was confirmed by densitometric analysis. Analysis of the PCR product from one kidney confirmed that it corresponded fully to the published sequence for rat bNOS.

For Series 2, Western analysis of proteins extracted from the outer cortex of kidneys of SHR and WKY rats demonstrated bands of mirunoreactivity corresponding to INOS and bNOS. A band for ecNOS was not consistently detected in the cortex. The expression of bNOS and INos immunoreactive proteins were increased 50–65% in the cortex of the SHR compared to the WKY.

For Series 3, the distribution of ecnOS and bNos imumuoreactivity in the kidney cortex of SHR and WKY corresponded to previous published series in Sprague-Dawley rats. The ecNOS immunoreactivity was readily demonstrable in the endothelium of arcuate arteries in the renal cortex of WKY and SHR. In WKY, inmunoreactivity was of a relatively modest intensity, whereas in SHR the immunoreactivity in the endothelium appeared more dense. Immunostaining for ecNOS was also apparent in endothelium of outer cortical arterioles, where it appeared to be less dense in WKY than in SHR. Using EM immunocytochemistry to assess ecNOS immunoreactive expression in glomerular capillary endothelium more quantitatively, the number of immiogold particles along the capillary walls of outer cortical glomeruli was significantly greater in SHR than WKY (SHR: 0.51±0.05, n=41, vs. WKY: 0.32±0.05, n=40, gold particles·μm$^{-1}$; p<0.01). Examination of bNOS immunoreactivity showed heavy staining of the macula densa cell plaque. There appeared to be less prominent stain in WKY compared to SHR. Kidneys from 5 SHR and 5 WKY rats were tested systematically for immunocytochemical staining. The results showed clearly stronger macula densa staining for bNOS in SHR compared to WKY in each pair examined by a blinded observer.

The baseline data for the micropuncture/microperfusion studies of rats of Series 4–6 are shown in Table 1. It is apparent that, compared to WKY, SHR rats were of similar body and kidney weight but had consistently higher levels of blood pressure and slightly greater heart rates. Tubuloglomerular feedback (TGF) parameters showed consistently higher values for proximal stop flow pressure during perfusion of the loop of Henle at 0 and 40 nl·min$^{-1}$ and a greater maximal TGF response, as assessed from differences between PSF during perfusion at 0 and 40 nl·min$^{-1}$ in SHR, which averaged 135% of the WKY control.

For Series 4, maximum TGF responses were contrasted in SHR and WKY rats during addition of vehicle or 7-NI to orthograde LH perfusates. As shown in Table 2, the maximum TGF responses were greater in SHR than WKY during perfusion of ATF+vehicle. The addition of 7-NI increased maximal TGF responses consistently in WKY by an average of 39% but had no significant effects on TGF responses of SHR.

For Series 5, TGF responses were contrasted in SHR and WKY during addition of L-arginine to orthograde LH perfusates. As shown in Table 3, the maximum TGF responses were greater in SHR compared to WKY during perfusion of ATF+vehicle. Addition of L-arginine significantly blunted ATF responses of WKY by an average of 18% but had no significant effects on TGF responses of SHR.

TABLE 1

Whole animal and kidney weights, mean arterial pressure (MAP), heart rate (HR), and tubuloglomerular feedback parameters in WKY and SHR rats used for functional studies

| Rat strain | No. of rats | No. of nephrons | Body weight (g) | Kidney weight (g) | MAP (mm Hg) | HR (min$^{-1}$) | PSF (mm Hg) during LH perfusion (nl · min$^{-1}$) at: | | |
|---|---|---|---|---|---|---|---|---|---|
| | | | | | | | 0 | 40 | 0 – 40 |
| WKY | 10 | 23 | 268 ± 8 | 1.17 ± 0.04 | 116 ± 3 | 354 ± 6 | 36.3 ± 0.5 | 28.0 ± 0.4 | 8.4 ± 0.3 |
| SHR | 13 | 32 | 266 ± 15 | 1.04 ± 0.06 | 158 ± 4 | 378 ± 8 | 41.0 ± 0.5 | 29.8 ± 0.4 | 11.2 ± 0.4 |
| p value | | | ns | ns | <0.001 | <0.05 | <0.001 | <0.01 | <0.001 |

Mean ± SEM values fran rats of series 4–6. PSF, proximal stop flow pressure.

TABLE 2

Values of proximal stop flow pressure (PSF) as a function of rate of orthograde perfusion of artificial tubular fluid (ATF) in SHR and WKY: Effects of 7-nitroindazole (7-NI) or renal perfusion pressure

| Rat strain | Added to ATF | No. of rats | No. of nephrons | MAP (mm Hg) | PSF (mm Hg) during retrograde LH perfusion (nl · min$^{-1}$) at: | | |
|---|---|---|---|---|---|---|---|
| | | | | | 0 | 40 | 0 – 40 |
| WKY | Veh | 4 | 8 | 121 ± 5 | 37.9 ± 0.8 | 28.4 ± 0.9 | 9.5 ± 0.5 |
| | 7-NI | 4 | 8 | | 38.1 ± 0.8 | 25.0 ± 1.2 | 13.2 ± 0.7 |
| p value | | | | | ns | <0.05 | <0.001 |
| SHR | Veh | 4 | 13 | 168 ± 11 | 41.3 ± 0.9 | 29.6 ± 0.6 | 11.8 ± 0.7 |
| | 7-NI | 4 | 13 | | 41.0 ± 1.0 | 29.3 ± 0.7 | 12.5 ± 0.6 |

Mean ± SEM values from series 4. Veh, vehicle; MAP, mean arterial pressure.

TABLE 3

Values of proximal stop flow pressure (PSF) as a function of rate of orthograde perfusion of artificial tubular fluid (ATF) in SHR and WKY: Effects of L-arginine

| Rat strain | Added to ATF | No. of rats | No. of nephrons | PSF (mm Hg) during LH perfusion (nl · min$^{-1}$) at: | | |
|---|---|---|---|---|---|---|
| | | | | 0 | 40 | 0 – 40 |
| WKY | Veh | 3 | 9 | 36.1 ± 0.7 | 28.4 ± 0.6 | 7.7 ± 0.8 |
| | L-arginine | 3 | 9 | 36.1 ± 0.7 | 29.8 ± 0.5 | 6.3 ± 0.4 |
| p value | | | | ns | ns | <0.05 |
| SHR | Veh | 4 | 9 | 41.1 ± 1.2 | 30.2 ± 1.1 | 10.4 ± 0.7 |
| | L-arginine | 4 | 9 | 41.0 ± 1.2 | 30.4 ± 0.7 | 10.6 ± 0.7 |
| p value | | | | ns | ns | ns |

Mean ± SEM values. Veh, vehicle.

For Series 6, TGF responses were contrasted in SHR and WKY during addition of the memtbrane-permeable nitroxide SOD mimetic, Tempol, to LH perfusates. As shown in Table 4, maximum TGF responses were again greater in SHR than WKY during retrograde perfusion of ATF+ vehicle. Addition of Tempol ($10^{-3}$ M) to the retrograde perfusions of ATF blunted TGF responses in SHR and WKY rats significantly. However, the blunting of TGF was significantly (p<0.01) greater in SHR than WKY. When normalized to the initial response, the percentage reduction in TGF with Tenpol was again greater in SHR (SHR: −26±2 vs. WKY: −17±3%; p<0.05).

In view of the findings from the examples, it is seen that the expression of both constitutive and inducible NOS isoforms are increased in the SHR kidney, and that the increase in constitutive NOS isoforms in the cortex and JGA appears to be transcriptionally regulated since it is accompanied by an increase in MRNA abundance. Despite this evidence of enhanced NOS expression in the JGA and/or the renal cortex, the TGF responses of SHR are exaggerated and are unresponsive either to local blockade of nNOS by microperfusion of 7-NI into macula densa or to local provision of NOS substrate by microperfusion of L-arginine into the macula densa. These enhanced responses persist after normalization of the renal perfusion pressure with a suprarenal aortic clamp and therefore are not a direct consequence of the elevated BP.

The results with the relatively bNOS-selective antagonist, 7-NI show that it has no effect on TGF responses of SHR despite potentiating TGF responses of WKY. Thus, the functional response to NOS inhibition is diminished in the SHR.

TABLE 4

Values of proximal stop flow pressure (PSF) as a function of rate of retrograde perfusion of artificial tubular fluid (ATF) in SHR and WKY: Effects of the nitroxide, superoxide dismutase mimetic, Tempol

| Rat strain | Added to ATF | No. of rats | No. of nephrons | PSF (mm Hg) during LH perfusion (nl · min$^{-1}$) at: | | |
|---|---|---|---|---|---|---|
| | | | | 0 | 40 | 0 – 40 |
| WKY | Veh | 3 | 10 | 34.9 ± 0.8 | 26.7 ± 0.7 | 8.1 ± 0.4 |
| | Tempol | 5 | 10 | 34.7 ± 0.8 | 28.0 ± 0.9 | 6.7 ± 0.4 |
| p value | | | | ns | ns | <0.05 |
| SHR | Veh | 5 | 10 | 40.3 ± 0.8 | 28.8 ± 0.6 | 11.5 ± 0.6 |
| | Tempol | 5 | 10 | 40.8 ± 0.8 | 32.1 ± 0.9 | 8.5 ± 0.8 |
| p value | | | | ns | <0.05 | <0.001 |

Mean ± SEM values. Veh, vehicle.

Microperfusion of L-arginine into the JGA blunted maximal TGF responses in WKY yet did not significantly modify responses in SHR. This implies that L-arginine delivery was not limiting for NO generation in the JGA of the SHR. This is consistent with previous findings that L-arginine does not lower BP or improve the glomerular filtration rate (GFR) of the SHR. The present findings indicate that a deficient delivery of L-arginine to the JGA cannot explain the enhanced TGF of outer cortical nephrons of SHR.

Tempol is a low molecular weight, nontoxic compound that equilibrates rapidly between extra- and intracellular compartments, thereby conferring much greater protection against post-ischemic cellular damage than SOD. Unlike other SOD mimetics, it is not dependent on metals and therefore is stable in the intracellular environment that contains high $Mg^{++}$ concentrations.

Because endothelium-dependent vasodilatation is impaired in the SHR, in vitro studies were done to further evaluate effect on endothelium-dependent vasodilatation.

In the first group, the short-term actions of TEMPOL were determined in anesthetized rats. Baseline mean arterial pressure (MAP) and renal vascular resistance (RVA) were significantly elevated in the SHR (n=6) compared to the WKY (n=6). The following data was obtained:

MAP: SHR=145±4 vs. WKY=118±3 mm Hg,

RVR: SHR=32±4 vs. WKY=10±8 mm Hg/ml/min.

TEMPOL was administered intravenously at 4 mg/kg and the animals tested

MAP: SHR=108±8 vs. WKY=98±6 mm Hg

RVR: SHR=17±2 vs. WKY=15±1 mm Hg/ml/min

TEMPOL 12 mg/Kg was given intravenously:

MAP: SHR=80±5 vs. WKY=99±7 mm Hg

The longer term effect of administration of TEMPOL at the rate of 250 mg/kg/day given intraperitoneally for 7 days showed TEMPOL had no effect on the MAP in WKY rats, but decreased MAP in the SHR from 133±2 to 120±3 mm Hg.

The finding that TEMPOL is effective in treatment of genetically-transmitted essential hypertension provides new treatment for forms of hypertension which have, hitherto, been difficult to treat. The following compositions are suggestions only and are not meant to limit the scope of the invention. Oral compositions may contain fillers and, additionally, preservatives along with other inert or active agents.

Composition #1 for Oral Use 500 mg. TEMPOL 500 mg. starch 5 mg. magnesium stearate.

The composition may be placed in capsules which may be enteric coated.

Composition # 2 for Parenteral Use 1 gram of TEMPOL is added to 500 ml of 5% glucose in half-normal saline for intravenous administration.

TEMPOL may be administered on a solid support. For example, patches for the administration of TEMPOL can be formulated as adhesive patches containing the drug. For example, the patch may be a discoid in which a pressure-sensitive silicone adhesive matrix containing the active agent may be covered with a non-permeable backing. The discoid may either contain the active agent in the adhesive or may have attached thereto a support made of material such as polyurethane foam or gauze that will hold the active agent. Before use, the material containing the active agent would be covered to protect the patch.

Composition #3 for Dermal Administration

A patch composed of trilaminate of an adhesive matrix sandwiched between a non-permeable backing and a protective covering layer is prepared in the following manner:

Two grams of TEMPOL is applied to 5 grams of a pressure-sensitive silicone adhesive composition BIOPSA™ Q7-2920 (Dow Corning Corp., Midland, Mich., U.S.A.). The adhesive is applied to a polyester film to provide in successive layers to provide about 200 mg of active agent per $cm^2$. The film containing the adhesive is then made into a patch of 10 $cm^2$. The patch is covered with a protective layer to be removed before application of the patch.

Patches may be prepared containing permeation enhancers such as cyclodextrin, butylated hydroxyanisole, or butylated hydroxytoluene. However, it should be remembered that the active agents of this invention are effective on application to the epidermal tissue. When the patches are to be applied to thin or abraded skin, there is little need to add a permeation enhancer.

What I claim is:

1. A method of treating a patient with essential hypertension comprising administration of a composition comprising as an active agent a blood pressure lowering effective amount of tempol in a pharmaceutically acceptable carrier.

2. A method of claim 1 wherein the composition is administered orally.

3. A method of claim 1 wherein the composition is administered transdermally.

4. A method of claim 3 wherein the composition is administered as a patch.

5. A method of claim 1 wherein the composition is administered parenterally.

6. A method of claim 5 wherein the composition is administered intravenously.

7. A method of claim 1 wherein the amount of tempol administered ranges from 10 to 300 mg/kg/day.

8. A method of controlling essential hypertension comprising the administration of 4-hydroxy-2,2,6,6-tetramethylk-1-piperidine-1-oxyl in an amount effective to lower the blood pressure of a patient having essential hypertension.

9. A method of claim 8, wherein said 4-hydroxy-2,2,6,6-tetramethyl-1-piperidine-1-oxyl is administered together with a pharmaceutically acceptable carrier.

10. A method of claim 8, wherein the amount of 4-hydroxy-2,2,6,6-tetramethyl-1-piperidine-1-oxyl that is administered ranges from 10 to 300 mg/kg/day.

* * * * *